United States Patent [19]

Varma et al.

[11] 4,248,783
[45] Feb. 3, 1981

[54] STEROIDS HAVING A 3-(4-HYDROXYPHENYL)PENTANEDIOIC ACID MONOHYDRAZIDE SUBSTITUENT

[75] Inventors: Ravi K. Varma, Belle Mead, N.J.; B. Richard Vogt, Yardley, Pa.

[73] Assignee: E. R. Squibb & Sons, Inc., Princeton, N.J.

[21] Appl. No.: 78,369

[22] Filed: Sep. 24, 1979

Related U.S. Application Data

[62] Division of Ser. No. 38,593, May 14, 1979.

[51] Int. Cl.$^3$ ............................................. C07J 71/00
[52] U.S. Cl. ..................... 260/239.55 D; 260/397.3; 260/397.5; 424/1
[58] Field of Search ............. 260/239.55, 397.3, 397.5, 260/239.55 D; /Steroids MS File

[56] References Cited

U.S. PATENT DOCUMENTS

| | | | |
|---|---|---|---|
| 3,940,475 | 2/1976 | Gross | 424/1 |
| 3,954,739 | 5/1976 | Wilkenson | 260/239.57 |
| 3,975,342 | 8/1976 | Gross | 260/112 R |

Primary Examiner—Elbert L. Roberts
Attorney, Agent, or Firm—Lawrence S. Levinson; Donald J. Barrack

[57] ABSTRACT

Steroids having as a substituent a group having the formula

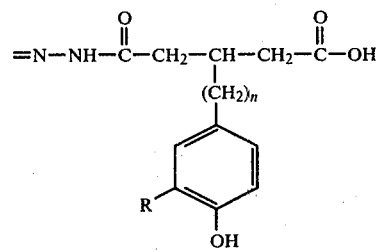

wherein R is hydrogen or alkyl and n is 0, 1, 2, 3 or 4 are useful as haptens and are also useful when radioiodinated as tracers in radioimmunoassays.

6 Claims, No Drawings

STEROIDS HAVING A 3-(4-HYDROXYPHENYL)PENTANEDIOIC ACID MONOHYDRAZIDE SUBSTITUENT

This is a division, of application Ser. No. 38,593, filed May 14, 1979.

RELATED APPLICATIONS

United States patent application Ser. No. 901,952, filed May 1, 1978, discloses steroid derivatives having the formula

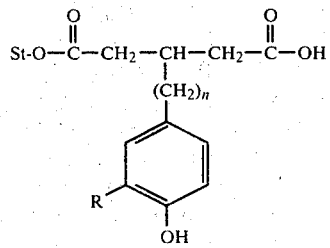

wherein St is a des-hydroxy steroid moiety of (i) a hydroxy steroid intended for radioimmunoassay or (ii) a hydroxy containing derivative of a steroid intended for radioimmunoassay, said derivative having a strong affinity for the antibodies of the steroid intended for radioimmunoassay; R is hydrogen or alkyl of 1 to 3 carbon atoms; and n is 0,1,2,3, or 4. It is disclosed that these steroids can be radiolabeled. The application also discloses anhydrides having the formula

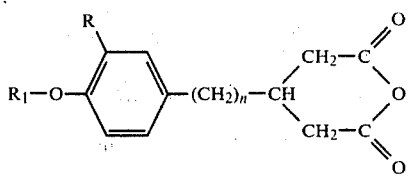

wherein R and n are as defined above, and $R_1$ is an alkanoyl group having 2 to 6 carbon atoms.

U.S. patent application Ser. No. 908,924, filed May 22, 1978, discloses steroid derivatives having the formula

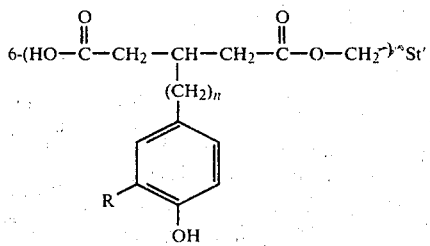

wherein St' is a 6-dehydro derivative of a 3-oxo-4,5-dehydro steroid intended for radioimmunoassay, said steroid being saturated in the 1,2-position, R is hydrogen or alkyl of 1 to 3 carbon atoms, and n is 0,1,2,3, or 4. It is disclosed that these steroids can be radiolabeled.

U.S. patent application Ser. No. 910,568, filed May 30, 1978, discloses vitamin $B_{12}$ derivatives having the formula

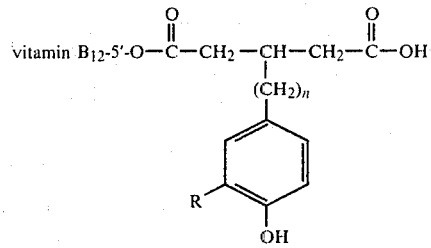

wherein R is alkyl of 1 to 3 carbon atoms and n is 0,1,2,3 or 4. It is disclosed that these vitamin $B_{12}$ derivatives can be radiolabeled.

BACKGROUND OF THE INVENTION

The measurement of various substances by the use of radioimmunoassay techniques has achieved widespread acceptance in recent years. Yalow and Berson, *In Vitro Procedures With Radioisotopes In Medicine*, International Atomic Energy Agency, Vienna (1970), pgs. 455 et seq., express the principle of radioimmunoassay in the following terms:

"Unlabeled antigen in unknown samples competes against labeled antigen ("tracer") for binding to antibody and thereby diminishes the binding of labeled antigen. The degree of competitive inhibition observed in unknown samples is compared with that obtained in known standard solutions for determination of concentration of antigen in unknowns."

Radioimmunoassay tests require a specific antibody, a radioisotope-labeled (hereinafter referred to as "radiolabeled") antigen, a pure sample of the antigen to be measured to serve as a reference standard, and means for the separation of free antigen from antibody-bound antigen. Radioimmunoassays follow the basic principle of saturation analysis, i.e., competition between labeled and unlabeled antigen for a fixed number of antibody binding sites.

When radiolabeled antigen, unlabeled antigen, and antibody are brought together, the amount of radiolabeled antigen bound to antibody and the amount of radiolabeled antigen remaining unbound (free) has a direct relationship to the amount of unlabeled antigen present when a given amount of antibody is present. Thus, by using a constant amount of antibody and radiolabeled antigen, and using known concentrations of unlabeled antigen, a standard (calibration) curve can be plotted showing antigen concentration versus the amount of radiolabeled antigen bound or versus radiolabeled antigen unbound, or versus a ratio of the two measurements. The concentration of antigen in an unknown sample can be read from the standard curve by determining the amount of bound or free radiolabeled antigen (or ratio of the two measurements) resulting when the unknown sample is mixed with the amount of radiolabeled antigen and antibody used to prepare the curve. In all radioimmunoassay procedures it is necessary to provide means for separating the bound from the free labeled tracer material. Many widely varied procedures have been developed and used; exemplary procedures are electrophoresis; chromatography; ion exchange; adsorption to dextran coated charcoal, talc, or cellulose; and a number of solid-phase antibody techniques.

The term "antigen", as used in the field of radioimmunoassays, may cover substances of limited immunogenicity (ability to generate antibodies). In those cases where the substance to be measured is of limited immunogenicity, the substance can be coupled with an immunogenic carrier, usually a protein, to increase its immunogenicity. A substance that is nonimmunogenic, but acquires immunogenicity when linked with a carrier is referred to as a "hapten".

Radioimmunoassay techniques have been used to determine the concentration in body fluids of various endogenous and exogenous steroids. In the development of radioimmunoassays for the various steroids, the preparation of a radiolabeled antigen is of primary concern. Possible radioisotope labels are tritium, carbon-14, iodine-125, iodine-131, and others. However, because tritium and carbon-14 must be counted by liquid scintillation (a time-consuming and expensive process), iodine-125 and iodine-131 are more desirable. For reasons well-recognized in the art (e.g., half-life, radiation hazard, counting efficiency and others) iodine-125 has become the radioisotope of choice for use in steroid radioimmunoassays.

The chemical structure of steroids is such that it is generally not possible to radioiodinate them directly. It is necessary, therefore, to utilize as a precursor of the radiolabeled antigen a derivative of the steroid to be assayed which can be readily iodinated. In choosing or developing such a derivative, the primary concern is the affinity of the derivative for the antibodies of the steroid to be assayed; the affinity of the derivative for the antibodies should, of course, be as close to the affinity of the steroid for the antibodies as possible.

BRIEF DESCRIPTION OF THE INVENTION

Compounds having the formula

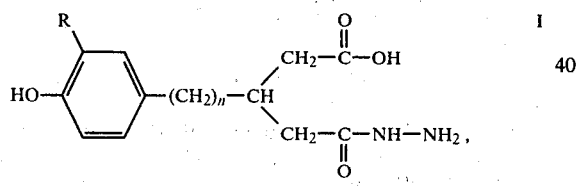

and the acid-addition salts thereof, are useful reagents for derivatizing organic compounds to permit the radioiodination of those compounds and their use as tracers in radioimmunoassays. Organic compounds derivatized with a reagent of formula I are also useful as haptens. In formula I, and throughout the specification, R is hydrogen or alkyl of 1 to 3 carbon atoms and n is 0,1,2,3 or 4.

The reagents described above contain a primary amino group, and therefore, react readily (in the presence of an organic or inorganic base) with organic compounds having an easily displaceable substituent. Compounds having a carbonyl group (including carboxylic acids, esters, amides, and halides; aldehydes; ketones; hemiketals; and hemiacetals) are particularly reactable with a reagent of formula I. A particularly preferred class of compounds which can be derivatized with a reagent of formula I are steroids containing an oxo group. Exemplary steroids are aldosterone, 6-ketoestradiol, 6-ketoestriol, progesterone, testosterone and cortisol.

Within the class of compounds described by formula I, the compound wherein R is hydrogen and n is O and its acid-addition salts are preferred.

DETAILED DESCRIPTION OF THE INVENTION

Reaction of a glutaric anhydride having the formula

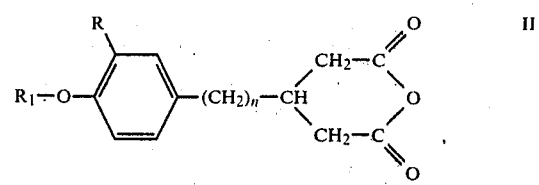

with hydrazine yields the corresponding product of formula I. The reaction can be run in an organic solvent, preferably an aprotic solvent such as tetrahydrofuran, and can conveniently be carried out at room temperature. The product of the reaction is highly hygroscopic and can be isolated as an organic or inorganic acid salt of formula I using conventional techniques. For example, the reaction product can be applied to a column of ion-exchange resin and the column eluted with an acid to yield the corresponding salt of a compound of formula I.

The glutaric anhydrides of formula II are disclosed in copending United States patent application 901,952, filed May 1, 1978, and in German Offenlegunsschrift No. 2,834,516 published Feb. 22, 1979. As disclosed therein, a glutaric anhydride of formula II can be prepared by first reacting a 4-methoxyphenyl aliphatic aldehyde having the formula

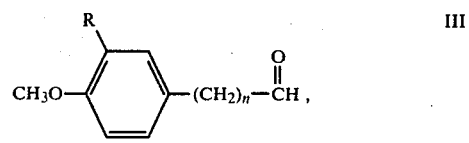

with at least 2 molar equivalents of cyanoacetic acid in the presence of a base (e.g., sodium hydroxide) to yield, on acid hydrolysis, a compound having the formula

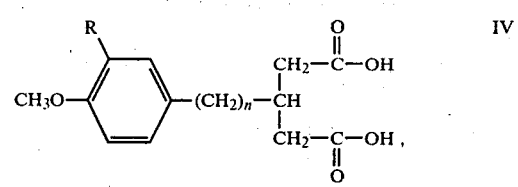

An alternative preparation for the compound of formula IV wherein n is O and R is hydrogen, i.e., 3-(4-methoxyphenyl)glutaric acid, is disclosed by Smith et al., J.A.C.S., 72, 1877 (1950). In that procedure, anisaldehyde is condensed with ethyl acetoacetate in the presence of piperidine to give ethyl anisal-bis-acetoacetate. Cleavage of this product to give the desired 3-(4-methoxyphenyl)glutaric acid can be accomplished with boiling alcoholic sodium hydroxide solution.

Demethylation of the glutaric acid derivatives of formula IV results in glutaric acid derivatives having the formula

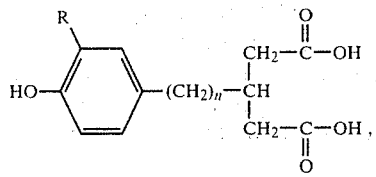

and can be accomplished by following one of the several procedures known in the art for the demethylation of aryl methyl ethers. One such procedure, described by Feutrill et al., *Aust. J. Chem.*, 25, (1972), involves the treatment of the aryl methyl ether with thioethoxide ion (readily prepared in situ from ethanethiol and sodium hydride) in a polar aprotic solvent, preferably dimethylformamide.

The phenolic hydroxy group of a compound of formula V can be protected with an alkanoyl group using art-recognized procedures. One such procedure comprises reacting the glutaric acid derivative with the appropriate acid anhydride (acetic anhydride is preferred). The preferred method of preparing a glutaric anhydride derivative of formula II from the glutaric acid derivative of formula V is to combine the conversion of the acid to anhydride and the protection of the phenolic hydroxy group into a single step. When the $R_1$ protecting group is acetyl, this would involve heating a glutaric acid derivative of formula V in acetic anhydride.

As stated above, a reagent of this invention (i.e., a compound of formula I or acid-addition salt thereof) can be reacted with any organic compound having an easily displaceable substituent to obtain a product which can be radioiodinated. The displacement reaction is particularly applicable to a compound containing a carbonyl group (i.e., $R_2=O$ wherein $R_2$ is an organic radical). Reaction of such a compound with a compound of formula I, or an acid-addition salt thereof, in the presence of an alcohol ($R_3$—OH, e.g., methanol), an inorganic base such as sodium acetate or sodium acetate in the presence of a weak acid such as glacial acetic acid yields an acid or ester having the formula

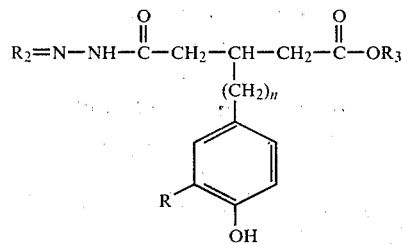

wherein $R_3$ is hydrogen or alkyl. An ester of formula VI can be saponified using procedures well known in the art. For example, the ester can be treated with a strong base. The saponified products form an integral part of this invention.

In some instances it will be desirable to react a hydrazide of formula I (or acid-addition salt thereof) with an organic compound containing more than one carbonyl group. Depending on the relative reactivity of the groups it may be necessary to block one of the groups using art-recognized techniques before reacting the compound with the hydrazide.

Before or after saponification, a compound of formula VI can be labelled ("tagged") with a radioisotope, preferably iodine-125 or iodine-131, using procedures well known in the art. Exemplary of methods known in the art is the method of Hunter and Greenwood; see *Nature*, 194:495 (1962). The radiolabeled haptens can be used as tracers in radioimmunoassay procedures following the general principles set forth in the Background of the Invention, supra. Exemplary detailed procedures are described in Jaffe et al., "Methods of Hormone Radioimmunoassay", Academic Press, New York (1974) and Berson et al., "Methods in Investigation and Diagnostic Endocrinology", Vol. 3 on "Steroid Hormones", North Holland, Amsterdam (1975). The radiolabeled haptens can also be used in automated radioimmunoassay systems, e.g., the system disclosed by Brooker et al. in U.S. Pat. No. 4,022,577, issued May 10, 1977.

The following examples are specific embodiments of this invention.

EXAMPLE 1

3-(4-Hydroxyphenyl)pentanedioic acid, monohydrazide, trifluoroacetic acid salt (A) 3-(4-Methoxyphenyl)glutaric acid A mixture of p-anisaldehyde (27.7 g), ethyl acetoacetate (52.1 g) and piperidine (4 ml) in 95% ethanol (10 ml) is stirred at room temperature for 5.0 hours while a solid forms. The solid is isolated by filtration, washed with 25% ethanol and crystallized from 95% ethanol to afford ethyl 2,2'-(4-methoxybenzal)-bis-acetoacetate (31.4 g), melting point 138°–141° C. The filtrate on dilution with an equal amount of water gives a solid which is crystallized from 95% ethanol to afford another crop of material (8.5 g), melting point 137°–142° C.

A mixture of ethyl 2,2'-(4-methoxybenzal)-bis-acetoacetate (30 g), ethanol (450 ml) and 50% sodium hydroxide (450 g) is refluxed vigorously for 1.0 hour. Water (150 ml) is added and most of the ethanol is removed by distillation in vacuo. The concentrate is acidified with concentrated hydrochloric acid and is extracted with ethyl acetate. The ethyl acetate solution is washed with brine, dried, evaporated and the residue is crystallized from benzene-methanol to afford 3.3 g of 3-(4-methoxyphenyl)glutaric acid, melting point 147°–150° C.

(B) 3-(4-Hydroxyphenyl)glutaric acid

To a stirred suspension of 57% sodium hydride-paraffin (6.45 g), in dry dimethylformamide (70 ml) is slowly added ethanethiol (11.89 ml) in dry dimethylformamide (20 ml). After stirring the resultant slurry for 15 minutes, a solution of 3-(4-methoxyphenyl)glutaric acid (3.0 g) in dry dimethylformamide (20 ml) is added. The slurry is heated in a bath at 165° C. for 5.0 hours and most of the solvent is removed by distillation in vacuo. The residue is diluted with water, acidified with concentrated hydrochloric acid and extracted twice with ether (the extracts are discarded). The solution is saturated with sodium chloride and extracted with ethyl acetate. The ethyl acetate solution is washed once with brine, dried and the residue crystallized from chloroform-hexane to afford 2.3 g of 3-(4-hydroxyphenyl)glutaric acid, melting point 168°–170° C.

(C) 3-(4-Acetyloxyphenyl)glutaric anhydride

A solution of 3-(4-hydroxyphenyl)glutaric acid (800 mg) in acetic anhydride (15 ml) is heated at 100° C. for 2.5 hours and evaporated to dryness in vacuo. The residual solid is crystallized from chloroform-hexane to afford 600 mg of 3-(4-acetyloxyphenyl)glutaric anhydride, melting point 140°–143° C.

(D) 3-(4-Hydroxylphenyl)pentanedioic acid, monohydrazide, trifluoroacetic acid salt To a solution of 3-(4-acetyloxyphenyl) glutaric anhydride (2.8 g, prepared as described above) in tetrahydrofuran (30 ml) is added 95% hydrazine (2.8 g) with stirring. The tetrahydrofuran is evaporated in vacuo and the residual syrup is diluted with water adjusted to pH 7.0 and applied to a column of polystyrene quarternary ammonium type anion exchange resin (30 g), which has been previously washed successively with 2 N sodium hydroxide and deionized water. The column is first eluted with deionized water (600 ml) to remove the neutral and basic impurities. The column is then eluted with 1 molar trifluoroacetic acid (1.5 l) in deionized water. The eluate is evaporated in vacuo at 40°–45° C. and the gummy residue is lyophilized to afford 3.4 g of the title compound.

EXAMPLE 2

3-(4-Hydroxyphenyl)pentanedioic acid, monohydrazide, hydrochloride

Following the procedure of Example 1, but substituting 1.0 M hydrochloric acid for trifluoroacetic acid, yields the title compound.

EXAMPLE 3

6-[2-[RS-4-Carboxy-3-(4-hydroxyphenyl)-1-oxobutoxy]hydrazono]estra-1,3,5(10)-triene-3,17$\beta$-diol

(A)

6-[2-[RS-4-Carboxy-3-(4-hydroxyphenyl)-1-oxobutoxy]hydrazono]estra-1,3,5(10)-triene-3,17$\beta$-diol, methyl ester A solution of 6-ketoestradiol (93 mg) and 3-(4-hydroxyphenyl)pentanedioic acid, trifluoroacetic acid salt (41 mg) in methanol (10 ml) containing sodium acetate (300 mg) and glacial acetic acid (0.1 ml) is refluxed for 20 hours. An additional portion of 3-(4-hydroxyphenyl)pentanedioic acid, trifluoroacetic acid salt (82 mg) is then added and the reaction is continued for 20 hours. The solution is then evaporated and dried in vacuo to a foamy solid. This is washed with water (three 3 ml portions) and the washings are discarded. After drying in vacuo, the residue is dissolved in a mixture of chloroform-methanol (9:1) and subjected to a preparative thin layer chromatography (tlc) on four pre-cooled silica gel plates (0.5×200×200 mm) using chloroform-methanol for development. The zone corresponding to the isomer mixture of the title compound is located under a U-V-lamp and isolated by extraction with chloroform-methanol (4:1) to afford 100 mg of the title compound, melting point 171°–186° C.

(B)

6-[2-[RS-4-Carboxy-3-(4-hydroxyphenyl)-1-oxobutoxy]hydrazono]estra-1,3,5(10)-triene-3,17$\beta$-diol A solution of the methyl ester prepared above (75 mg) in 70% methanol containing 3 M sodium hydroxide (0.6 ml) is stirred under an atmosphere of nitrogen for 5.0 hours; the starting material disappears. The solution is adjusted to pH 4.5 by the addition of acetic acid, the methanol is evaporated in a stream of nitrogen and diluted with brine (3.0 ml). The mixture is cooled briefly in an ice-bath, the solids are isolated by filtration, washed twice with water (0.5 ml portions) and dried in vacuo at 60° C., yielding 58 mg of the title compound.

EXAMPLE 4

3RS-3,16$\alpha$,17$\beta$-Trihydroxyestra-1,3,5(10)-triene-6-one,[4-carboxy-3-(4-hydroxyphenyl)-1-oxobutoxy]hydrazone,methyl ester

(A)

3RS-3,16$\alpha$,17$\beta$-Trihydroxyestra-1,3,5(10)-triene-6-one,[4-carboxy-3-(4-hydroxyphenyl)-1-oxobutoxy]hydrazone A solution of 6-ketoestriol (100 mg) and 3-(4-hydroxyphenyl)pentanedioic acid, monohydrazide (250 mg) in methanol (7.0 ml) containing sodium acetate (250 mg) and glacial acetic acid (0.1 ml) is refluxed for 20 hours; the starting steroid is consumed. The solvents are evaporated in vacuo, the residue is diluted with water and filtered to isolate the solids. The filtrate is extracted with ethyl acetate, the extracts are combined, evaporated and the residue is mixed with the solids isolated above. This is stirred with a dichloromethane-methanol mixture (4:1, 20 ml) and filtered to remove the insoluble solids. The filtrate is concentrated and applied on two preparative tlc plates of silica gel (1.0×200×200 mm). The plates are developed with dichloromethane-methanol (9:1) and the major band (more polar than the starting steroid) encompassing the stereoisomers of the title compound is extracted with dichloromethane-methanol (7:3) to afford 110 mg of the title compound, melting point 70°–84° C. The product is a mixture of the syn and anti isomers at the 6-position.

(B)

3RS-3,16$\alpha$,17$\beta$-Trihydroxyestra-1,3,5(10)-triene-6-one,[4-carboxy-3-(4-hydroxyphenyl)-1-oxobutoxyl]hydrazone A solution of the methyl ester (43 mg) in 85% methanol (2.6 ml) is adjusted to pH 10 to 11 with 3 M sodium hydroxide. The solution is then stirred at room temperature for 24 hours and adjusted to pH 4.0 by the addition of acetic acid. The mixture is transferred to a tapered centrifuge tube and most of the solvents are removed initially in a stream of nitrogen and finally in vacuo. The residue is mixed with a saturated sodium chloride solution (2.0 ml), titurated, cooled briefly in an ice bath and centrifuged. The supernatant liquid is removed by decanting and this washing procedure is repeated once again on the residual solid. The tube is dried in vacuo at 40° C. and extracted with four 5 ml portions of a dichloromethane-methanol mixture (9:1). The extracts are combined, concentrated to about 2.0 ml, diluted with dichloromethane (2.0 ml) and applied to a column of silica gel (5.0 g). The column is eluted successively with dichloromethane and dichloromethane-methanol (95:5 and 8:2) to afford in the last solvent mixture 32 mg of the title compound, melting point 287°–295° C.

EXAMPLE 5

3RS-Pregn-4-ene-3,20-dione,3-[4-carboxy-3-(4-hydroxyphenyl)-1-oxobutyl]hydrazone A solution of progesterone (188 mg), 3-(4-hydroxyphenyl)pentanedioic acid, trifluoroacetic acid salt (100 mg), sodium acetate (88 mg) and acetic acid (0.1 ml) in methanol (4.0 ml) is stirred at room temperature for 36 hours. The resulting solution is transferred to a tapered centrifuge tube and evaporated, initially in a stream of nitrogen and then in vacuo at 40° C. The residue is washed twice with a saturated sodium chloride solution (3.0 ml portions) titurated, centrifugated and decanted. The tube is dried in vacuo at 40° C. and the solids are washed with four 5.0 ml portions of dichloromethane-methanol (4:1). The washings are combined, concentrated and applied on two silica gel plates (1.0×200×200 mm). The plates are developed with dichloromethane-methanol (9:1). The band encompassing the stereoisomers of the title compound (more polar than the starting steroid) is located under u.v. light and extracted with dichloromethane-methanol (4:1) to afford 110 mg of the title compound, melting point 184°–186° C.

EXAMPLE 6

3RS-Pregn-4-ene-3,20-dione,20-[4-carboxy-3-(4-hydroxyphenyl)-1-oxobutyl]hydrazone During the tlc purification of the compound described in Example 5, another band more polar than the former is located on the plate. This is isolated by extraction with dichloromethanemethanol (8:2) to afford 23 mg of the title compound melting point 180°–185° C.

EXAMPLE 7

11β,18-Epoxy-18,21-dihydroxypregn-4-ene-3,20-dione,20-[4-carboxy-1-oxo-3-(4-hydroxyphenyl)-butyl]hydrazone

(A) 21-[[(1,1-Dimethylethyl)dimethylsilyl]oxy]aldosterone,18,20-hemiacetal

To a solution of aldosterone (108 mg) in dry dimethylformamide (2.5 ml) is added successively t-butyldimethylchlorosilane (105 mg) and imidazole (82 mg). The resulting solution is stirred at room temperature for 1.5 hours, added to water (20 ml) containing acetic acid (0.1 ml) and extracted with dichloromethane (three 20 ml portions). The extracts are combined, washed with water, dried, evaporated and dried in vacuo. Tituration of the residue with hexane affords 115 mg of crystals of the title compound, melting point 158°–159° C.

(B) 21-[[(1,1-Dimethylethyl)dimethylsilyl]oxy]-18-RS-[(trimethylsilyl)oxy]aldosterone To a solution of the hemiacetal prepared above (110 mg) in dry dimethylformamide (3.0 ml) is added successively freshly distilled trimethylchlorosilane (101 mg) and imidazole (120 mg). The resulting solution is stirred at room temperature for 20 hours, added into water (20 ml) containing acetic acid (0.1 ml) and extracted with dichloromethane (three 20 ml portions). The extracts are combined, washed with water, dried, evaporated and dried in vacuo to afford the title compound as a glass (122 mg).

(C) 21-[[(1,1-Dimethylethyl)dimethylsilyl]oxy]-18RS-[(trimethylsilyl)oxy]aldosterone,3-[4-carboxy-3-(4-hydroxyphenyl)-1-oxobutyl]hydrazone A solution of the silyl derivative prepared above (505 mg) and 3-(4-hydroxyphenyl)pentanedioic acid, trifluoroacetic acid salt (500 mg) in methanol (12.0 ml) containing triethylamine is stirred at room temperature under an inert atmosphere for 20 hours. The mixture is evaporated in vacuo and the residue is washed successively with water (30 ml) containing acetic acid (1.5 ml) and water (10 ml) and dried in vacuo. It is dissolved in dichloromethane and absorbed on a column of silica gel (20 g). The column is eluted successively with dichloromethane and dichloromethane-methanol (98:2 and 4:1) to afford the starting steroid (325 mg) and, in the methanol-containing fractions, the title compound (200 mg) as a solid.

By repeating the reaction once again on the recovered starting steroid (325 mg) but using sodium acetate (300 mg) instead of triethylamine, another 270 mg of the title compound is obtained.

(D) 11β,18-Epoxy-18,21-dihydroxypregn-4-ene-3,20-dione,[4-carboxy-1-oxo-3-(4-hydroxyphenyl)butyl]hydrazone A solution of the above compound (470 mg) in 70% acetic acid (30 ml) is stirred at room temperature for 4.0 hours. The acetic acid and water are removed by distillation in vacuo at room temperature. The resulting solid is dissolved in the minimum amount of methanol and applied to a silica gel column (30 g). The column is eluted successively with dichloromethane-methanol mixtures (95:5, 9:1 and 4:1). The earlier fractions give some aldosterone and some unreacted starting steroid. The later fractions are a mixture of the starting material and the title compound as indicated by monitoring the fractions by tlc. The later fractions are combined, evaporated and subjected to chromatography once again on a column of silica gel (10 g) to isolate successively the unreacted starting steroid and the title compound (167 mg). This material is dissolved in methanol by warming, and the methanol solution is concentrated to 1.3 ml and diluted with ice-water adjusted to pH 4.0 with hydrochloric acid. The solid that separates is isolated by filtration and dried in vacuo to afford 128 mg of the title compound.

The nmr spectrum of the above material shows that it is a mixture of 4-isomers. An accurate melting point can not be determined because even at 400° C. it does not melt, but develops a blackish brown color indicating decomposition before melting.

What is claimed is:

1. A steroid having as a substituent a group having the formula

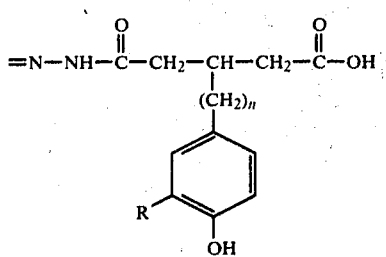

wherein R is hydrogen or alkyl and n is 0, 1, 2, 3 or 4.

2. The steroid in accordance with claim 1 having the name 6-[2-[RS-4-Carboxy-3-(4-hydroxyphenyl)-1-oxobutoxy]hydrazono]estra-1,3,5(10)-triene,3,17β-diol.

3. The steroid in accordance with claim 1 having the name 3RS-3,16α,17β-trihydroxyestra-1,3,5(10)-triene-6-one,[4-carboxy-3-(4-hydroxyphenyl)-1-oxobutoxy]-hydrazone.

4. The steroid in accordance with claim 1 having the name 3RS-pregn-4-ene-3,20-dione, 3-[4-carboxy-3-(4-hydroxyphenyl)-1-oxobutyl] hydrazone.

5. The steroid in accordance with claim 1 having the name 3RS-pregn-4-ene-3,20-dione,20-[4-carboxy-3-(4-hydroxyphenyl)-1-oxobutyl]hydrazone.

6. The steroid in accordance with claim 1 having the name 11β,18-epoxy-18,21-dihydroxypregn-4-ene-3,20-dione,20-[4-carboxy-1-oxo-3-(4-hydroxyphenyl)butyl]-hydrazone.

* * * * *